United States Patent
Woltjer et al.

(10) Patent No.: US 12,156,766 B2
(45) Date of Patent: Dec. 3, 2024

(54) ROBUST, SIMPLE, AND EFFICIENTLY MANUFACTURABLE TRANSDUCER ARRAY

(71) Applicant: NovioScan B.V., Nijmegen (NL)

(72) Inventors: Reinout Woltjer, Utrecht (NL); Bastianus Theodorus Johannes Alberts, Nijmegen (NL)

(73) Assignee: NovioScan B.V., Nijmegen (NL)

( * ) Notice: Subject to any disclaimer, the term of this patent is extended or adjusted under 35 U.S.C. 154(b) by 0 days.

(21) Appl. No.: 17/777,072

(22) PCT Filed: Nov. 20, 2020

(86) PCT No.: PCT/EP2020/082983
§ 371 (c)(1),
(2) Date: May 16, 2022

(87) PCT Pub. No.: WO2021/099618
PCT Pub. Date: May 27, 2021

(65) Prior Publication Data
US 2022/0401072 A1 Dec. 22, 2022

(30) Foreign Application Priority Data
Nov. 22, 2019 (NL) .................... 2024291

(51) Int. Cl.
*A61B 8/00* (2006.01)
*B06B 1/06* (2006.01)

(52) U.S. Cl.
CPC .......... *A61B 8/4494* (2013.01); *B06B 1/0607* (2013.01); *A61B 8/4488* (2013.01)

(58) Field of Classification Search
CPC .... A61B 8/4494; A61B 8/4488; B06B 1/0607
See application file for complete search history.

(56) References Cited

U.S. PATENT DOCUMENTS

| 5,559,388 A | 9/1996 | Lorraine et al. |
|---|---|---|
| 5,567,657 A | 10/1996 | Wojnarowski et al. |

(Continued)

FOREIGN PATENT DOCUMENTS

| EP | 0219171 A2 | 4/1987 |
|---|---|---|
| EP | 2459322 B1 | 11/2014 |

(Continued)

OTHER PUBLICATIONS

Schiavone et a.l: "A highly compact packaging concept for ultrasound transducer arrays embedded in neurosurgical needles", Microsyst Technol (2017) 23:3881-3891, Published online: Jan. 18, 2016, DOI 10.1007/s00542-015-2775-1, article is published with open access at Springerlink.com.

*Primary Examiner* — J. San Martin
(74) *Attorney, Agent, or Firm* — N.V. Nederlandsch Octrooibureau (57) ABSTRACT

A transducer array for ultrasound applications includes a plurality of transducer elements that are provided with self-aligned connections to a flexible cable. The array is easy to manufacture and suited for wearable, wireless, and other small ultrasound devices. A simple and efficient method of producing a robust transducer array involves at least partially separating the transducer elements after their connection to their respective conductors.

20 Claims, 5 Drawing Sheets (56) References Cited

U.S. PATENT DOCUMENTS

| | | | |
|---|---|---|---|
| 5,617,865 A | 4/1997 | Palczewska et al. | |
| 5,703,400 A | 12/1997 | Wojnarowski et al. | |
| 5,722,137 A | 3/1998 | Lorraine et al. | |
| 5,865,163 A | 2/1999 | Wildes et al. | |
| 5,920,972 A | 7/1999 | Palczewska et al. | |
| 5,923,115 A | 7/1999 | Mohr, III et al. | |
| 6,541,896 B1 | 4/2003 | Piel, Jr. et al. | |
| 6,580,034 B2 | 6/2003 | Daane et al. | |
| 6,651,318 B2 | 11/2003 | Buck et al. | |
| 6,734,362 B2 | 5/2004 | Buck et al. | |
| 6,994,674 B2 | 2/2006 | Sheljaskow et al. | |
| 7,229,292 B1 | 6/2007 | Haider et al. | |
| 7,804,970 B2 * | 9/2010 | Hippe | B06B 1/0622 310/334 |
| 8,347,483 B2 | 1/2013 | Guo | |
| 8,528,174 B2 | 9/2013 | Harhen et al. | |
| 2002/0073781 A1 | 6/2002 | Hashimoto et al. | |
| 2004/0254471 A1 | 12/2004 | Hadjicostis et al. | |
| 2008/0134793 A1 * | 6/2008 | Woychik | G01D 11/245 250/208.2 |
| 2012/0179044 A1 * | 7/2012 | Chiang | A61B 8/54 600/467 |
| 2013/0068382 A1 | 3/2013 | Harhen et al. | |
| 2014/0145561 A1 * | 5/2014 | Jin | G10K 11/002 174/255 |
| 2018/0228462 A1 | 8/2018 | Maghsoudnia et al. | |

FOREIGN PATENT DOCUMENTS

| | | |
|---|---|---|
| EP | 2723506 B1 | 2/2017 |
| JP | S5666992 A | 6/1981 |

\* cited by examiner

ROBUST, SIMPLE, AND EFFICIENTLY MANUFACTURABLE TRANSDUCER ARRAY

FIELD OF THE INVENTION

The present invention is in the field of transducer arrays for ultrasound applications, such as those used for wearable, wireless ultrasound devices. It also relates to a robust, simple, and efficient method of producing said transducer array, and a product comprising said transducer array.

BACKGROUND OF THE INVENTION

Ultrasound is an oscillating sound pressure wave with a frequency greater than the upper limit of the human hearing range (hence ultra-sound). Ultrasound devices may operate with frequencies from 20 kHz up to several gigahertz. Ultrasound may be used in many different fields. Ultrasonic devices are used to detect objects and measure distances. Ultrasonic imaging (sonography) is used in both veterinary medicine and human medicine. In the non-destructive testing of products and structures, ultrasound is used to detect invisible flaws. Industrially, ultrasound is used for cleaning and for mixing, and to accelerate chemical processes. At higher power levels, ultrasound may be useful for medical treatment or for changing the chemical properties of substances.

There have been approaches to improve ultrasound systems in terms of size, cost, and quality, such as transducer design, transmit and receive circuitry design and beamforming algorithms. Currently, a significant percentage of the size and power of an ultrasound system is devoted to the beamformer, which is responsible for directing and/or focusing the ultrasound beam. A standard transducer array with beamformer, which consists of 64 to 128 transmit/receive channels, is straightforward to implement if design constraints such as size and power are relaxed. As ultrasound systems become more portable, or even wearable, it seems necessary that new beam-former architectures with fewer channels and lower power consumption than standard cart-based systems are required.

An application of ultrasound concerns bladder monitoring. Many people such as elderly persons, children with dysfunctional voiding or bedwetting, women after delivery of a baby, patients with a neurogenic bladder, demented people, and others, have a difficulty to control functioning of the bladder, and to be at the toilet on time to urinate. This (partial) incontinence is highly inconvenient and may lead to psychological problems and physical problems (e.g. infection, local skin problems). Solutions to such incontinence include the application of e.g. diapers and bedwetting alarms. However, such after-the-event solutions can limit the consequences of incontinence but do not always provide the best solution for certain groups of patients.

For some ultrasound applications, such as bladder monitoring, dedicated hand-held devices are used. These dedicated devices suffer from various drawbacks, amongst others a need of a wire between transducer and monitor, handheld use of the device; hence they are not suited for long-term monitoring. Some prior art devices may require a trained professional to handle the transducer and to evaluate what is seen. Typically, these are used for intermittent examinations in a healthcare setting such as a hospital. With current technologies it is not possible to keep continuously track of bladder filling and alarm a user or his/her caretaker when the bladder becomes full. That is relevant for a number of (health) problems, including, but not limited to Urinary Incontinence (UI) in children (hypo- or hyperactive bladder, dysfunctional voiding, bedwetting); adults with neurogenic bladder dysfunction, people with temporary or permanent spinal problems, in nursing home patients. It is also relevant for the prevention of Urinary Retention (UR) (e.g. peri- and post-operatively, post-partum).

Ultrasound devices are typically hand-held and built for intermittent use. They are also large, or at least too large to be wearable, they cannot be fixed to the body (semi-) permanently, cannot be used by a patient during normal life, during sitting, standing or lying down, and may require cabling for power- and signal transport, and are not practical in use.

For certain devices using ultrasound for determining or monitoring a liquid volume in a cavity, such as in a body, the ultrasound may need to be provided at an angle relative to an orientation of the device. Especially bones, such as the pubic bone near the bladder, may obstruct ultrasound; the device then typically needs to be placed above the pubic bone, and needs to transmit and receive ultrasound at an angle.

In general, for prolonged use devices, and in particular small wearable devices, such as a bladder monitor, need to use minimal amounts of energy, as typically the power source is "on board" of the device and it should be recharged as little as possible. Electronic circuits of the prior art ultrasound technology are dedicated to obtain as much and as detailed information as possible, typically using sophisticated electronics and software enabling imaging. However, energy consumption of such devices is relatively large. This is not much of a problem if such devices are wired to the grid but it may be a significant problem, in view of operation time, for stand-alone devices.

The prior art devices, and in particular transducer arrays, are difficult and cumbersome to produce. Often connections to individual transducer elements in the array need to be provided by soldering individual contacts. This soldering is typically limited to about 0.3 mm width, below which dimension the cost of soldering increases significantly. The soldering of transducer elements at a small pitch implies a risk of short-circuiting between neighbouring transducer elements, and as a consequence ruining the performance of the array. This is further complicated by the need to use coaxial cabling, since for conventional image forming, the transducer element must generally be driven by powerful electronic circuits located remotely from the transducer array.

Attempts have been made to use e.g. soldering machines or wire bonding machines such as those used in the semiconductor field. These machines typically use pressure and/ or heat to achieve soldering, which as a consequence deteriorates or ruins characteristics of the piezoelectric transducer material. As a consequence, no practical applications are found.

Attempts to properly align connections have also been made. However, the skilled person is typically limited to the above soldering, of each and any connection, and proper alignment of the connections is therewith at least complex, if not impossible. This alignment, of course, is even more cumbersome for larger arrays or for smaller pitches.

Therefore, there remains a need for a robust, simple transducer array which may be used in an ultrasound device, which overcomes one or more of the above disadvantages, without jeopardizing essential functionality and advantages.

SUMMARY OF THE INVENTION

The present disclosure relates in a first aspect to a robust, simple, efficiently manufacturable transducer for ultrasound comprising a transducer array of at least n transducer elements, wherein n is preferably greater than 8, wherein adjacent transducer elements are provided with at least partial first separations therebetween, wherein said partial separations may be provided by a slicer, such as a dye slicer, a dye saw or a laser cutter. A flexible cable comprising at least n conductors, preferably a flat flex cable, is provided for attaching to the transducer elements. At least two of the conductors are electrically connected to at least two of the individual transducer elements by a self-aligned electrical contact. Preferably all of the electrically connected contacts are connected at once, such as using a soldered contact provided by a soldering machine, preferably at least 3 to 1024 transducer elements are connected at once, optionally including at least one ground contact. The conductors provide connections to an electrical power source and/or an electrical circuit, for supply of signals, such as electrical pulses, for driving the respective transducer elements. The electrical connections may comprise at least one contact, typically at an other side of a respective conductor of the flexible cable.

Furthermore there may be provided a casing for the transducer array, in which casing the transducer array can be provided, preferably in which casing the transducer array is embedded. Typically, the casing fully surrounds the transducer array, optionally with an opening or window for the ultrasound, or to allow a cable to be connected to the exterior. Preferably however, no cable is provided to the exterior and the device is wireless, with all electronics being provided, within the casing. By the coincidence of a number of different factors, the presently configured device can achieve its objectives of simplification especially for low resolution purposes. Firstly, by choosing for low resolution, a limited array of less transducer elements can be easily manufactured in a monolithic structure. Secondly, by giving in on image quality, reducing the amount of electronics. Thus the power required for driving and processing such an array is reduced, allowing the necessary electronics to be included within the casing of a small device that can be worn. Consequently, cabling and connection is simplified, since there is no longer a need for shielded coaxial cables to connect the transducers to external processing electronics.

In addition to the transducer array and the cable, the casing may thus comprise a printed circuit board (PCB) carrying all necessary interconnections, a microprocessor provided with the required processing capability to drive the array, a memory for temporarily or permanently storing data and instructions, a wireless communication module for communicating data and instructions with an external receiver e.g. by wifi, bluetooth or the like and a power source such as a battery, which may be replaceable or rechargeable. The skilled person will well understand that some or all of these items may be separate or integrated together as appropriate.

The electrical contacts are self-aligned, which in the present context means that individual contacts are not individually connected one at a time to discrete transducer elements but instead joined collectively and subsequently separated by sawing or the like. In the presently described method one common contact may be applied, which one common contact is subsequently provided with separations. This electrical contact can either be made by soldering, by using conductive glue, or nonconductive glue, in which case the electrical contact will be a capacitively coupled contact, or variations of these contacting techniques.

In a second aspect, the present disclosure relates to an ultrasound device comprising a simplified transducer array, comprising transmission control electronics for beam steering of the array comprising at least one high-voltage pulse source, wherein sources are linked to a low-voltage timing circuit for timing of the at least one pulse sources, and/or receiving control electronics simplified to limit energy consumption when processing received ultrasound. The receiving control electronics is preferably selected from (i) at least one and preferably all ultra-sound receiving transducer element are adapted for determining ultrasound energy in connection with a rectifying amplifier and the rectifying amplifier in connection with an analogue adder for adding the outputs of the rectifying amplifiers, (ii) <50%, preferably <20%, of the n transducer elements are connected or connectable to receiver electronics, optionally with delays enabling beam steering in reception, and (iii) combinations thereof, and/or wherein the transducer elements are capable of operating separately, sequentially, in phase-shift mode, in parallel mode, in frequency scan mode, in spatial scan mode, in intensity mode, in pulsed mode, in harmonic mode, variations thereof, or combinations thereof.

In a third aspect the present disclosure relates to a product comprising an ultrasound device or a simplified transducer array, wherein the product is preferably selected from a wearable device, a portable device, a medical device, a non-destructive testing device, or combinations thereof, such as a small wireless ultrasound device for signalling a change in a body tissue, body vessel or body cavity, such as a bladder, preferably a stand-alone device, and/or comprising a positioner for maintaining the product in a position, preferably at least one sensor for determining posture of a body of a user, a contacting means for contacting the product to a skin of the body, an energy scavenger, an ADC for converting analogue array signals to digitized output signals, wherein the product is wearable and is substantially flat, and/or comprising a movement sensor, such as an accelerometer, gyroscope, and a magnetic sensor.

In a fourth aspect the present disclosure relates to a method of producing a robust, simplified transducer array, comprising providing a plate of transducer material with conductive contacts on both sides, providing at least n conductors in a flexible cable, wherein n is preferably greater than 8. At one side of the plate, connecting by soldering, or gluing or other contacting means, a single connecting strip or contact with the ends of the conductors and over a width of the plate. During this process the temperature of the plate is preferably maintained below 220° C., preferably below 200° C., such as 180° C., preferably at 10° C. or more below a temperature at which de-poling of the transducer material may occur. After providing the single contact, the transducer material is divided into an array of at least n transducers by providing at least n−1, at least partial separations or grooves at the side of the contact. The separations fully extend through the soldering thereby dividing the single electrical contact into n separate self-aligned electrical contacts, each contact being in connection with an individual conductor of the flexible cable, and placing the divided and connected transducer material into a casing. The transducer material may be fixed within the casing, such as by gluing, by epoxy kit, by bonding, by applying a mechanical force, and variations or combinations thereof.

The present transducer array, when used for e.g. a bladder monitor, provides deep penetration of ultrasound into the body, with a not too high ultrasound frequency (approximately 2 MHz) to limit the attenuation in the body. Further, beam steering allows the beam to be pointed towards the bladder in each person. At least +/−45-degree angles are provided to enable measurements on a bladder lying deep behind the pubic bone. The pitch of the phased array transducer elements can be small, such as 0.4 mm at maximum (for a 2 MHz transducer), which is found to avoid side lobes radiating in other directions. For this application, the dimensions of the phased array transducer are typically at least 10 mm (for a 2 MHz transducer) which is found to limit the divergence of the ultrasound beam. A minimum number of transducer elements is typically 20, and a maximum is typically 32. The area of the transducer is typically large enough to generate sufficient ultrasound power to enable deep penetration into the body.

It is noted that for various applications a reduction in detail of information obtained by the transducer array is acceptable. This is the case, for instance, for non-imaging applications. Recognizing a volume of a cavity and/or an amount of liquid in said cavity is found to be achievable in combination with the above significant reduction in components and in energy consumption.

The present array may comprise an array of n*m transducers elements operating at a frequency of 20 kHz-50 MHz, typically 100 kHz-20 MHz, preferably 500 kHz-15 MHz, wherein at least two neighbouring transducer elements are at a mutual distance of approximately 0.5 wavelength (0.5λ±10%), preferably 0.5λ±5%, more preferably 0.5λ±3%, preferably comprising at least 1*n transducers, transmission control electronics for beam steering of the array comprising at least one high-voltage pulse source, wherein sources are linked to a low-voltage timing circuit for timing of the at least one pulse sources, receiving control electronics adapted to limit energy consumption when processing received ultrasound, and an electrical power source in electrical connection with the array or an electrical connection for providing electrical power to the array. The array may be relatively small, with less components than used in prior art ultrasound imaging, limiting energy consumption and component count, and may comprise one or more rows m. As arrays may be relatively small, a space occupied by said arrays can also be relatively small. The rows of arrays, if applied for e.g. a bladder scan, are oriented such that a phased array provides beam steering at an angle relatively to the longitudinal axis of the row(s). For addressing the transducers in a phase mode, and for receiving and addressing receiving arrays, a controller is provided. The controller may perform further functions. The present invention optionally makes use of energy reduction measures to reduce energy consumption when processing received ultrasound.

The present product can use the simplified phased array to enable beam steering at arbitrary angles at low energy and lower complexity and cost than prior art products. In an exemplary embodiment said product is a small, typically wearable, wireless ultrasound device for signalling a change in a body tissue, body vessel or body cavity, such as a bladder, preferably a stand-alone device.

In the context of the present disclosure the term "small" in combination with the present product relates to a size, indicating that the present product may be worn for a prolonged period of time without relevant discomfort for a user thereof and that it is preferably (nearly) invisible when worn under clothes. The term "wireless" indicates that there is no electrical conductor connecting the present product to an outside world; the term "wearable" indicates that a user of the product can move freely during use. As a consequence of the product being small, wearable and wireless it can be worn and likewise is portable and wearable e.g. without limiting movement of the user. Further, a body cavity relates to a fluid (liquid/gas)-filled space in an animal or human other than those of vessels (such as blood vessels and lymph vessels). Further, position is taken to be a general term for a configuration of the human body, whereas the term posture relates to an (un)intentionally or habitually assumed body position. Typical positions are e.g. standing, sitting, squatting, crouching, kneeling, lying. Other positions, such as atypical positions and stress positions fall under the term as well, but are considered less relevant as these latter positions typically occur less often. The term "(semi-)continuously" is used to indicate that monitoring and signalling can take place over a prolonged period of time; during said period of time at any given moment monitoring/signalling may occur; however, typically during said period of time the product is in an idle mode at least part of the time; it preferably is taking active measurements only at specific and selected moments. In view of "calculating" it is noted that often a precise outcome is questionable; in such cases the term may refer to "estimating".

The present device or product can for instance be used for permanent and semi-permanent measurements. It can also be connected to a body in ultrasound contact in a permanent or semi-permanent mode; thereto contacting means should preferably be compatible with a human skin, e.g. in terms of toxicity, irritation, adhesion, form stable over time, etc.

Details of such a bladder monitoring product, use thereof, and method of operating can be found in WO 2016/085341 A2, of which the specification and claims are incorporated herein by reference.

Thereby the present invention provides a solution to one or more of the problems of the prior art.

Further advantages are detailed throughout the description.

DETAILED DESCRIPTION OF THE INVENTION

The present disclosure relates in a first aspect to a robust, simple, efficiently manufacturable transducer array for ultrasound beam steering according to the claims.

In an exemplary embodiment of the present transducer array each individual transducer element may comprise a piezoelectric material selected from titanates, bulk piezo material, piezocomposite material active piezoelectric material, such as lead zirconate titanate (PZT) (Pb[ZrxTi1-x]O3 0≤x≤1), AlN, (PbMg0.33Nb0.67)1-x(PbTiO3)x, preferably with x=0.28-0.5 (PMNT), Cobalt MNT, ceramic and crystalline material, a Microelectromechanical system (MEMS), such as a CMUT and PMUT, and combinations thereof.

In an exemplary embodiment of the present transducer array the transducer element material may have a thickness of 0.1 mm to 2 mm, such as 0.3 mm to 1.0 mm.

In an exemplary embodiment of the present transducer array at least one transducer element may be provided with a conducting material for electrical contact, preferably a coated conducting material, preferably selectively on a top and bottom side thereof.

In an exemplary embodiment of the present transducer array transducer elements in the array may be separated by a spacing, preferably an air-filled spacing, wherein the spacing has a width of 0.01 mm to 1 mm, such as 0.05 mm and where the separations or grooves between the individual elements extend preferably 50% to 95% of the element thickness i.e. of the thickness of the plate of transducer material. It has been found that for non-imagining ultrasound applications, there may be no need for complete mechanical separation of individual transducers. The presently proposed partial separation of transducer elements by providing grooves in a plate that leave an intact region is thus adequate for such purposes as volume estimation or position/size determination. This is because cross-talk and interference between partially attached transducer elements is not sufficient to cause problems of accuracy.

In an exemplary embodiment of the present transducer array a ground contact may be provided which extends from a contact at a bottom side of the transducer material, preferably at an unseparated side, along at least one side of the transducer material, to at least one part of the contact on the top side of the transducer material.

In an exemplary embodiment of the present transducer array the casing may comprise a polymer, such as polycarbonate or acrylonitrile butadiene styrene (ABS) or polypropylene. A thickness of the casing through which the ultrasound is transmitted is preferably from 0.01 mm to 2 mm.

In an exemplary embodiment of the present transducer array the rear side of the transducer may be protected by an optional layer over the transducer that gives mechanical stiffness, protects the transducer in the casing and/or serves as an acoustical backing layer.

In an exemplary embodiment of the present transducer array the casing may comprise space holders for determining a thickness of a matching layer, for example a ¼λ matching layer.

In an exemplary embodiment of the present transducer array the casing may be part of an ultrasound path. The ultrasound path may include one or more of: an acoustical layer, an acoustical matching layer, an acoustical lens, or an acoustical prism. The array may be arranged to emit ultrasound through the first surface at which the transducer elements are separated from each other. In a preferred embodiment, the array is arranged to emit ultrasound through the second surface, usually where the ground electrode is located. The transducer elements are not separated from each other at this second surface as the grooves have not penetrated fully through the plate. The acoustic backing layer may serve as a structural support to hold the free ends of the transducer elements in a stable manner.

In an exemplary embodiment of the present transducer array the array may comprise from 10 to 1024 transducer elements, preferably from 12 to 256 transducer elements, more preferably from 14 to 128 transducer elements, even more preferably from 16 to 64 transducer elements such as from 20 to 32 transducer elements. In particular, for non-imaging applications where the volume or size of an object must be determined, a lower number of transducer elements may be more than sufficient.

In an exemplary embodiment the present phased array transducer may comprise at least one series of m transducer elements over a length, wherein each of the electrodes on one side or all m transducer elements are connected electrically to the respective transducer electronics, and wherein the (counter-) electrodes on the other side are i) all connected together, or ii) the electrodes on the other side are split in two halves, where half of each electrode length is connected to a first electrode connector and the other half electrode length is connected to a second electrode connector. This may allow separate activation of the two halves, e.g. applying two different acoustic lenses (e.g. prisms or focusing lenses) on these two separate halves of the transducer array. In a further alternative iii) a fractions of the electrode length are connected to respective electrode connectors. The electrode length is preferably divided into 2, 3, 4 or 5 fractions, perpendicular to the length direction of the transducer elements. This allows even more different possibilities for control of the transducer elements e.g. as lenses. As a fourth possibility, iv) combinations of the above may be implemented.

In an exemplary embodiment of the transducer array, transducer elements may have a pitch of 40 microns to 800 microns, preferably 70 microns 700 microns, more preferably 100 microns to 500 microns, such as 300 microns to 500 microns.

In an exemplary embodiment of the present transducer array transducer elements may operate at a frequency of 20 kHz to 50 MHz, preferably 500 kHz to 10 MHz.

In an exemplary embodiment of the present transducer array at least two neighbouring transducer elements may be at a mutual distance of approximately 0.5 wavelength (λ±10%).

In an exemplary embodiment of the present method and device, the side of the transducer that has been sawn or otherwise separated, may be protected by an optional layer over the transducer for providing mechanical stiffness, protection of the transducer in the casing, and optionally serving as an acoustical backing layer.

In an exemplary embodiment of the present method the soldering or gluing or the connecting strip may have a width of 0.2 mm to 2 mm, measured in the direction from the first end surface towards the second end surface. It may be applied to the conductors at an end of a flex cable.

In an exemplary embodiment of the present method the transducer material may cooled during soldering, such as cooled 10° C. or more below a temperature at which de-poling of the transducer material may occur. Additionally or alternatively, soldering may be applied during less than 10 seconds.

In a further exemplary embodiment of the present method, after soldering, the ends of the connecting cables may be bent, such as bent over the casing, or bent to create space for the separation process.

In an exemplary embodiment of the present method a ground contact may be provided which extends from a contact at a rear side or second surface of the transducer material, along at least one side of the transducer material, to at least one conducting part of the top side or first surface of the transducer material, wherein the at least one conducting part of the top side is in electrical contact with at least one of the conductors of the flexible cable.

The disclosure also relates to a use of a device or product as herein described for determining or monitoring a liquid volume in a cavity, such as a bladder, a uterus (amniotic fluid), a sinus, a pleural cavity, a pericardial sac, and a vessel such as an aorta, for detecting or monitoring at least one of aneurism, infection, tumour, dehydration, pleural effusion, urine influx rate from at least one kidney, hydrocephalus, a size of a human or animal cavity, for determining a liquid volume in a lung, for training, for ultrasound image forming, as a flow sensor, for (semi)continuous monitoring over longer periods of time, for monitoring during normal life, and for monitoring inside or outside a hospital or (long-term) caretaking environment. The skilled person will recognise that the device may optionally be operated in combination with one or more further) devices to achieve the above-mentioned functions.

In an exemplary embodiment the present phased array transducer may comprise one high-voltage pulse transmission source per transducer, wherein the sources are preferably identical.

In an exemplary embodiment the present phased array transducer may comprise a voltage controller for applying a voltage to the transducer.

In an exemplary embodiment of the present transducer array connected or connectable receiving transducer elements are selected such that a number of not-connected transducer elements are provided in between the connected transducer elements. There may be from 1 to 7, preferably from 2 to 6, more preferably between 3 and 5 non-connected elements between each pair of adjacent connected elements. In the case that this value is 3, the largest side lobes in transmit directionality are compensated by a minimum in the receive directionality, making this choice optimal in certain cases.

The invention is further detailed by the accompanying figures and examples, which are exemplary and explanatory of nature and are not limiting the scope of the invention.

DETAILED DESCRIPTION OF FIGURES

Figure 1:
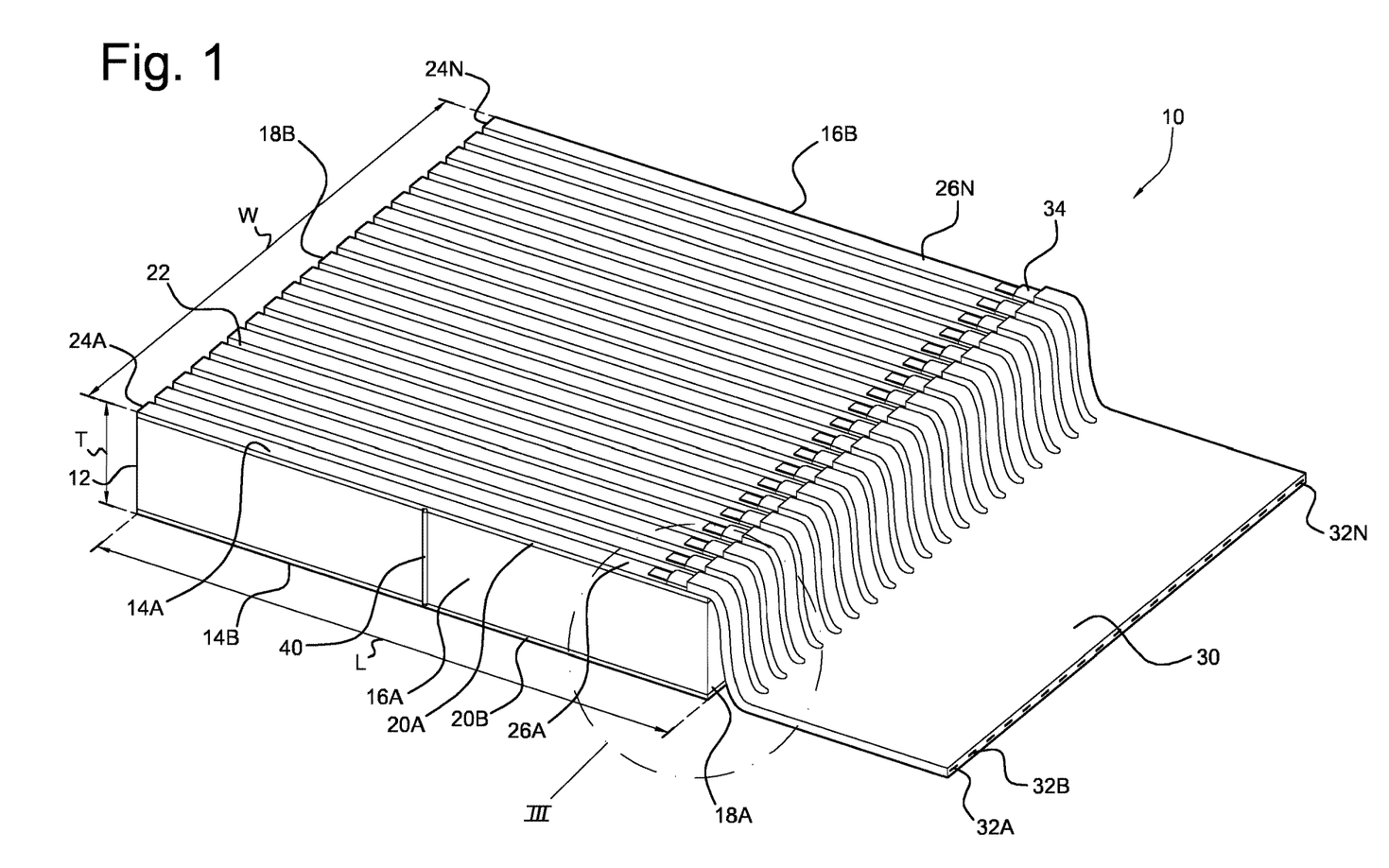
FIG. 1. shows a perspective view of an ultrasound array.

FIG. 1 shows in perspective view a transducer array 10 for ultrasound application. The transducer array 10 comprises a plate 12 formed of transducer material and having opposed first and second surfaces 14A, 14B, with first and second side faces 16A, 16B, and first and second end faces 18A, 18B therebetween. The first and second surfaces 14A, 14B are provided with respective first and second electrode layers 20A, 20B.

An electrical cable 30 comprising a plurality of parallel conductors 32A-N, is connected electrically to the first electrode layer 20A by a single contact in the form of a connecting strip 34 extending transversally to the cable 30 over a width W of the plate 12.

The plate 12 is provide with grooves 22 extending along the first surface 14A from the first end face 18A to the second end face 18B, the grooves 22 extending through the first electrode layer 20A and into the transducer material to a depth sufficient to divide the plate 12 into an array of n transducer elements 24A-N, each having an individual first electrode 26 A-N and sharing as a common second electrode, the second electrode layer 20B. The grooves 22 extend through the single contact in the form of a connecting strip 34 to also separate one conductor 32A from an adjacent conductor 32B, whereby each conductor 32A-N is connected to a respective individual first electrode 26A-N.

The transducer material in the illustrated embodiment is a piezoelectric material comprising lead zirconate titanate, $(Pb[Zr_{0.52}Ti_{0.48}]O_3)$ although other known alternatives may also be applied. The plate 12 has a length L of 40 mm, a width W of 20 mm and a thickness t of 1 mm. The electrodes layers 20A, 20B are silver of micron thickness although they have been indicated as considerably thicker merely for illustrative purposes. The cable 30 is a 20 pin flex cable of 0.5 mm pitch with 0.25 mm copper conductors 32 stripped back to have 2 mm of bare copper for connection to the first electrode layer 20A.

Also illustrated in FIG. 1 is a ground contact 40 extending from the second electrode layer 20B to the first surface 14A of the plate across the first side face 16A and electrically connected to the individual first electrode 26A of the first transducer element 24A adjacent to the first side face 16A.

Although referred to as the first transducer element 24A, this transducer element has its respective first and second electrodes effectively shorted by the ground contact 40 and cannot thus operate as a transducer element. This first transducer element 24A is thus used as a connection to the common second electrode layer 20B and to the first conductor 32A of the cable 30.

Figure 2:
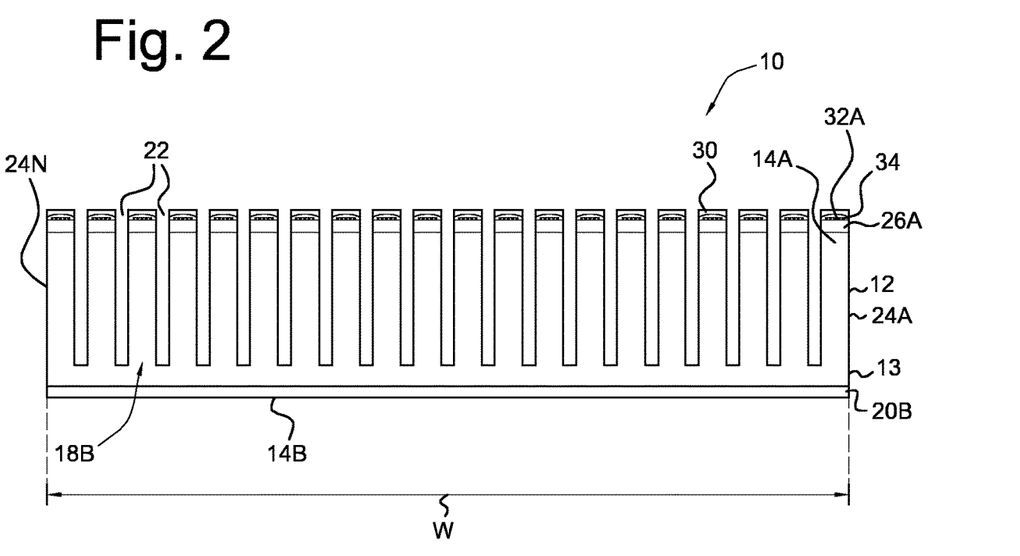
FIG. 2: shows an end elevation of the array of FIG. 1.

FIG. 2, is an end elevation of the transducer array 10 of FIG. 1 viewed towards the second end face 18B. The transducer elements 24 can be seen separated by grooves 22. The grooves 22 have a width of 50 microns and a depth of 0.9 mm. They are applied at a pitch of 0.5 mm, such that the individual transducer elements 24 have a width of around 0.45 mm.

With reference to the first transducer element 24A, each transducer element has a similar construction. Starting from the first surface 14A, the transducer element 24A comprises a portion of conductor 32A extending from the cable 30. Beneath the conductor 32A is the connecting strip 34. The connecting strip 34 is formed of a 62/36/2 Sn/Pb/Ag solder having a low melt temperature of 179 C to avoid approaching the Curie temperature of the piezo material. The 2% silver avoids the possibility of the silver electrode layer 20A dissolving during processing. It will also be understood that the solder of the connecting strip 34 may no longer be identifiable as a distinct layer as it will have flowed around the conductor 32A.

Beneath the connecting strip 34 is the individual first electrode 26A above the piezoelectric material of the plate 12. At the lowermost portion of the first transducer element 24A, an intact region 13 of the plate 12 is not cut or separated and still extends across the full width W of the transducer array 10. This intact region 13 has a thickness of around 80 microns, which has been found sufficient to ensure adequate stability of the structure. Beneath the intact region 13 is the second electrode layer 20B, which serves as a common second electrode for the first transducer element 24A and all of the other transducer elements 24B to 24N.

Figure 3:
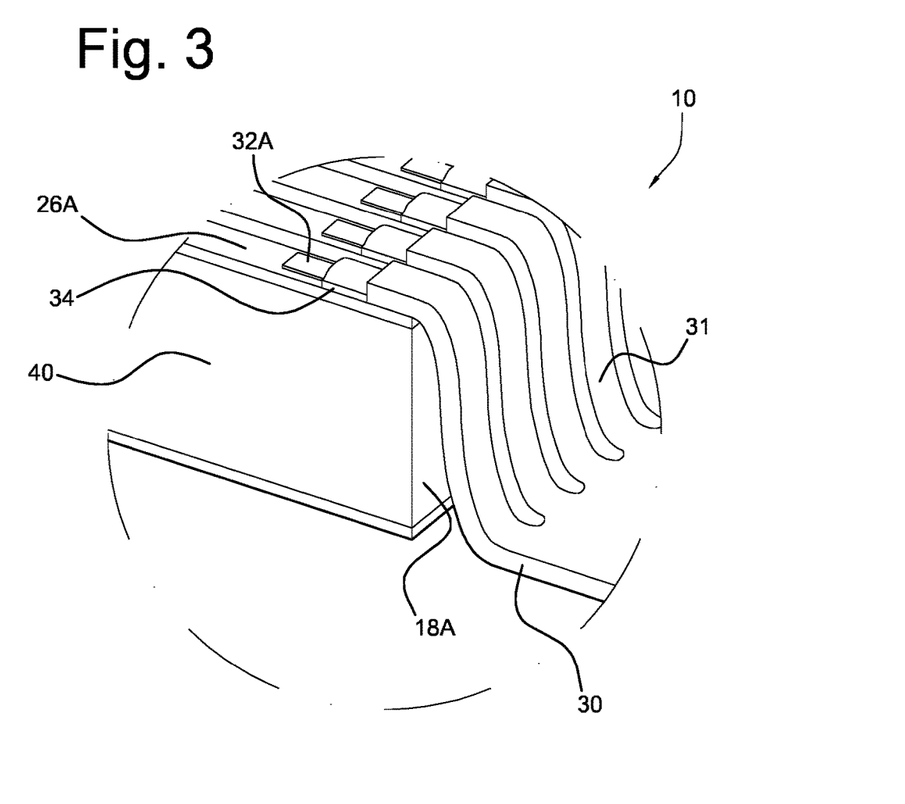
FIG. 3: shows a detail taken at III of the array of FIG. 1.

FIG. 3 is a detail of part of the array 10 of FIG. 1 at III. In this detail, the manner in which the cable 30 is bent downwards adjacent to the first end face 18A can better be seen. This allows the grooves 22 to also partially cut into the insulation 31 surrounding the conductors 32A-N. It can also be seen how the conductors 32A-N and the connecting strip 34 only extend a short distance in the length direction of the array. Also visible is the ground contact 40, which connects the second electrode layer 20B to the individual first electrode 26A and the first conductor 32A of the cable 30.

Figure 4:
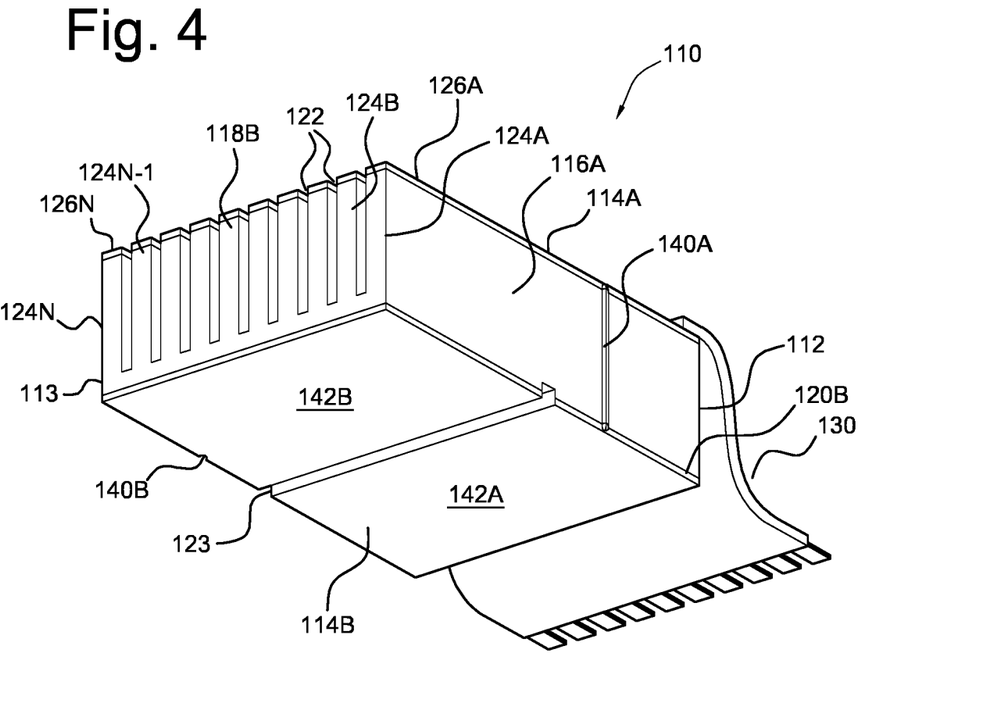
FIG. 4: shows a perspective view of an array according to a second embodiment.
Figure: shows a side elevation of the array of FIG. 4.

In FIG. 4, a perspective view from the underside of an alternative implementation of an array 110 is presented, showing the first side face 116A and the second end face 118B. In this embodiment, like elements to the previous figures are referenced with similar reference numerals preceded by 100. This second embodiment has first and second ground electrodes 142A, 142B at the second surface 114B. The ground electrodes 142A, 142B may be formed by cutting or ablating through the second electrode layer 120B in a direction perpendicular to the grooves 122 at the first surface 114A. In the illustrated embodiment, the plate 112 has been cut through by a secondary separation 123 to the depth of the intact region 113 such that the grooves 122 are also visible through the secondary separation 123.

To connect each of the ground electrodes 142A, 142B at the second surface 114B to one of the individual first electrodes 126A-N at the first surface 114A, there are provided first and second ground contacts 140A, 140B. In this manner, the ground electrodes 142A, 142B can be connected with the cable 130 via the first and last individual first electrodes 126A, 126N. This is convenient as it allows all of the electrical connections to be arranged via one cable 130.

Figure 5:
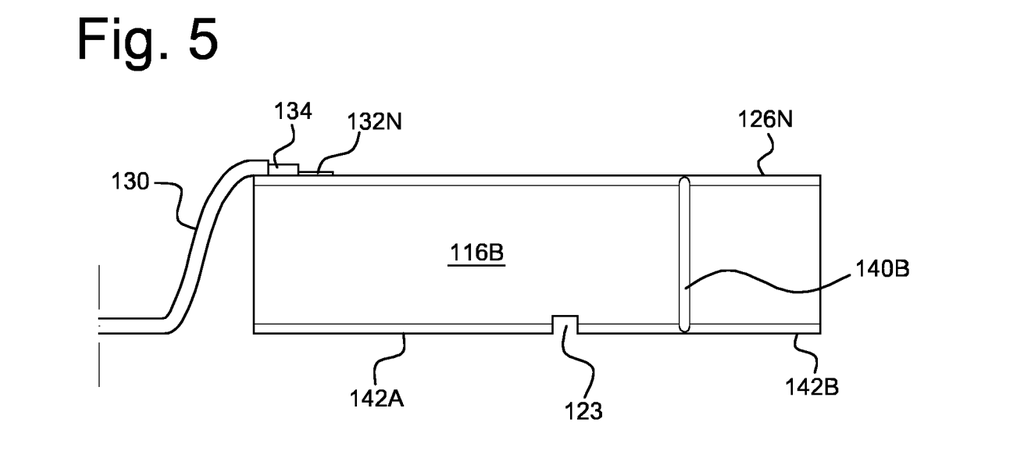

FIG. 5 shows in side elevation, the array 110 of FIG. 4, viewed towards the second side face. In this view, the second ground contact 140B is visible, extending between the second ground electrode 142B and the last individual first electrode 126N, whence it connects to the last connector 132N of the connecting strip 134 of cable 130.

The second embodiment of FIGS. 4 and 5 depicts an array of ten transducer elements 124A-N, separated by nine grooves 122. In this case, although the first and last elements 124A, 124N are referred to as transducer elements, they are in fact inoperative, since their contacts are shorted by the respective first and second ground contacts 140A, 140B. The remaining eight transducer elements 124B-124N−1 are connected with respectively two ground contacts 142A, 142B at the bottom side and one first electrode 126B-126N−1 each at the top side, enabling separate activation of two sections of each transducer element 124B-124N−1.

Figure 6:
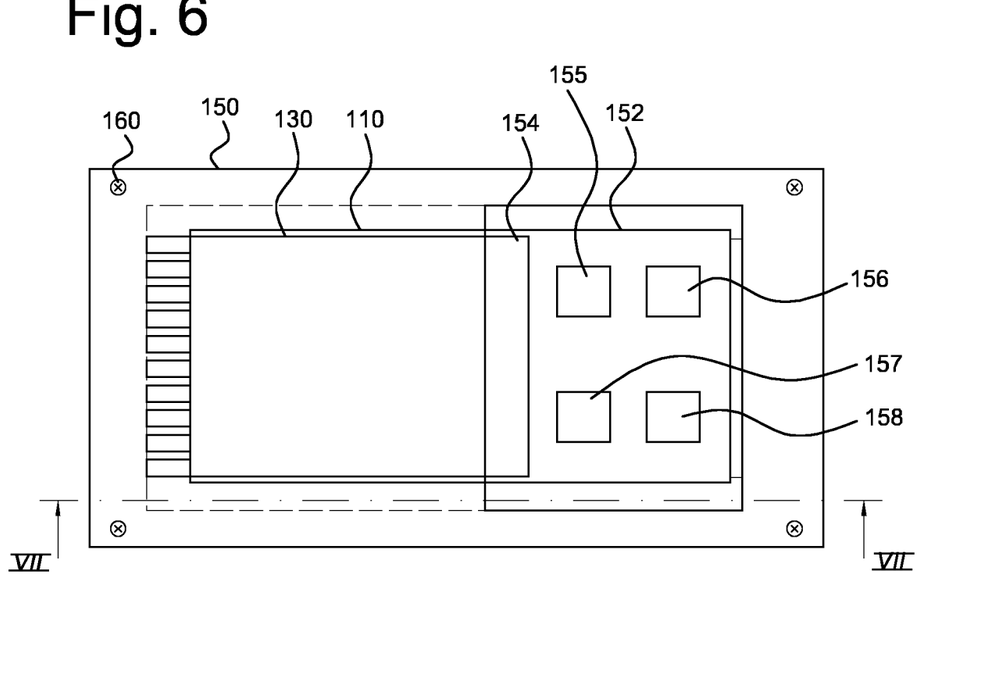
FIG. 6: shows a plan view of the array of FIG. 4 mounted in a casing.

FIG. 6 shows a plan view of the array 110 of FIGS. 4 and 5 embedded in a casing 150. The cable 130 is attached to a printed circuit board (PCB) 152 at a ZIF (zero insertion force) connector 154. The PCB 152 supports a microprocessor 155 provided with the required processing capability to drive the array 110, a memory 156 for storing data and instructions, a wireless communication module 157 for communicating data and instructions and a battery 158. In the illustrated embodiment, the casing is of polycarbonate although ABS plastic is also suitable. The casing is held together with screws 160.

Figure 7:
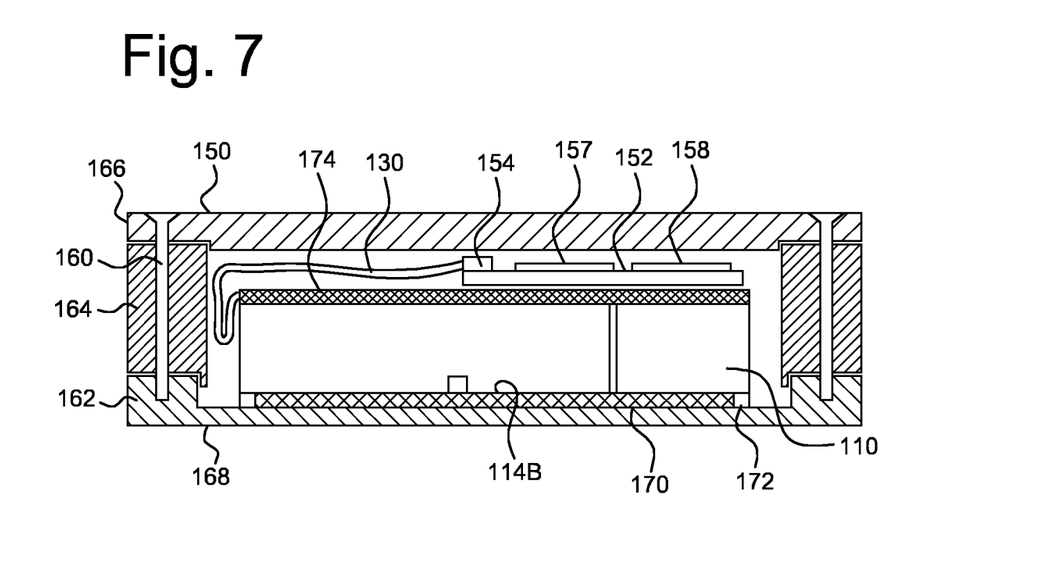
FIG. 7: shows a cross-section through the device of FIG. 6 taken along line VII-VII.

FIG. 7 shows a cross-section taken through the casing 150 of FIG. 6 in the direction VII-VII. As can be seen, the casing 150 is formed in three parts, comprising a base plate 162, a ring 164 and a cover 166.

The base plate 162 includes a window region 168, of reduced thickness, against which the second surface 114B of the array 110 is located. In order to ensure good coupling, the array 110 is spaced from the window region 168 by a matching layer 170. Spacers 172 forming part of the casing 150 are provided to ensure a correct thickness of the matching layer.

It will be understood that the transducer can alternatively be mounted directly into the casing using epoxy, with only the casing material for acoustical matching.

The first surface 114A of the array 110 is covered with an acoustic backing layer 174. The backing layer 174 is a magnetic rubber tape material that is glued to the first surface of the array 110. Barium ferrite synthetic rubber tape has been found most suitable for this purpose. It not only makes an excellent acoustical backing but also serves to stabilise the free ends of the separated transducer elements.

Figure 8:
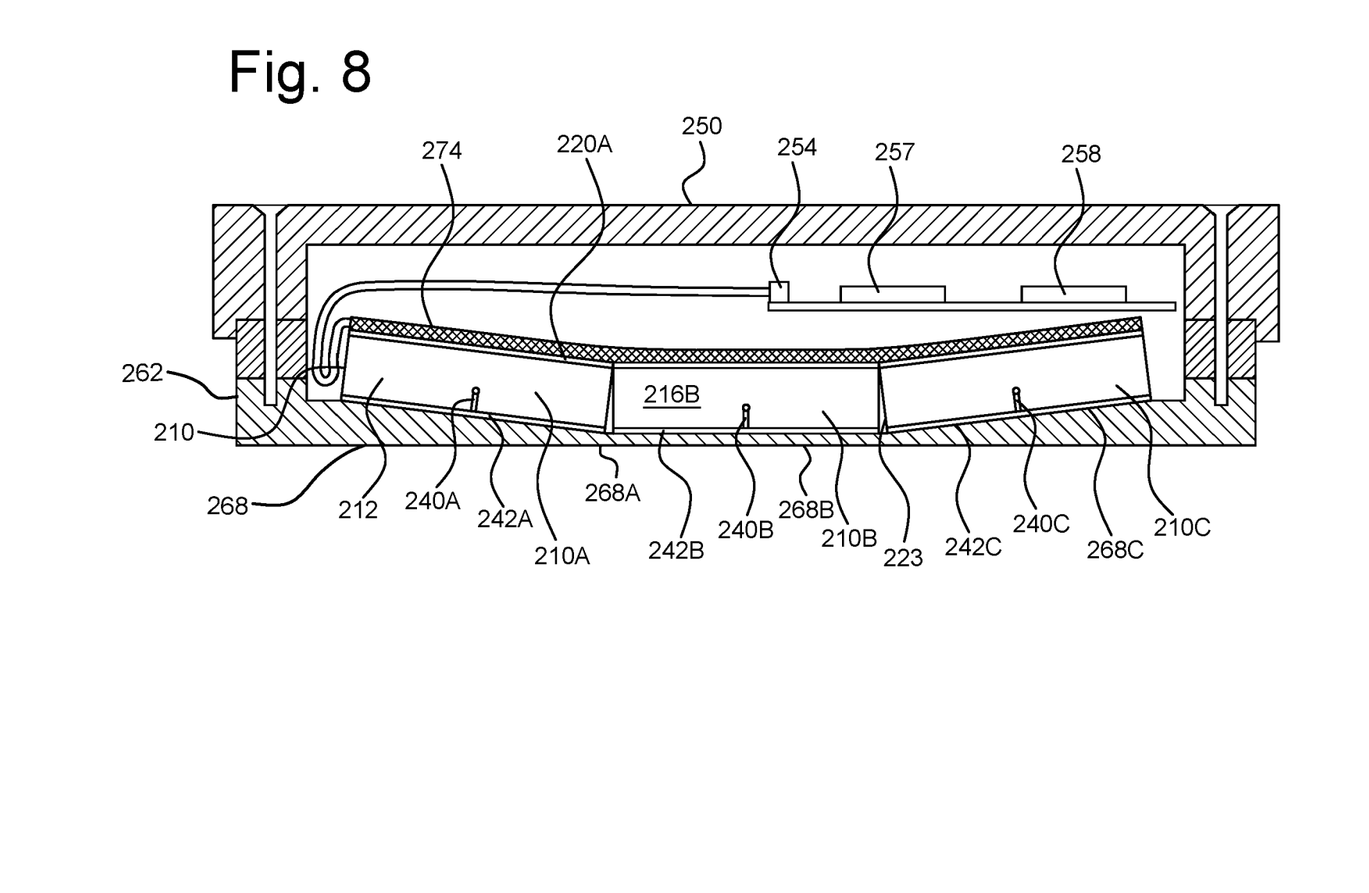
FIG. 8: shows a device including an array according to a third embodiment in a similar cross-section to FIG. 7.

FIG. 8 shows in a cross section similar to that of FIG. 7, the second face 216B of a third embodiment of an array 210 in which like elements to earlier embodiments are provided with similar reference numerals preceded by 200.

The array 210 is mounted in a housing 250 and connected via connector 254 to communication module 257 and battery 258. The array 210 is similar to the previous embodiment but in this case, the array 210 is divided in the length direction into three sections 210A, 210B and 210C by secondary separations 223, which extend through the full thickness of the plate 212. The secondary separations extend to the first electrode layer 220A. In actual fact, the secondary separation can be cut to just short of this layer and then the remaining portion of piezo material can be carefully broken. This preferably takes place after application of the rubber acoustic backing layer 274, which serves to maintain the integrity of the array 210 once the three sections 210A-C have been broken apart. Each section 210A-C has its own respective ground electrode 242A-C. In this embodiment however the ground electrodes 242A-C have respective ground contacts 240A-C that can be connected by conventional solder connections to ground terminals (not shown) within the casing 250.

The secondary separations 223 allow the three sections 210A-C to be angled with respect to one another for directional transmission of the ultrasound. To this end, the window region 268 also has three regions 268A, 268B, 268C. The inner surface of the central second window region 268B is parallel to the lower surface of the base plate 262. The first window region 268A is angled by 4 degrees away from the second window region 268B, while the third window region 268C is angled by 4 degrees in the opposite direction. In this case, the second surface 214B of the array 210 is coupled directly to the base plate 262 without any matching layer or spacers.

Although in this third embodiment, the three sections 210AC of the array 210 are angled to one another, it will be understood that the advantages of three such sections that can be separately driven can also be achieved without angling the sections or without complete separation. Acoustic prisms may be implemented within the casing to achieve a similar effect.

The invention although described in detailed explanatory context may be best understood in conjunction with the accompanying examples and figures and in particular, the following embodiments.

1. A transducer array for ultrasound application, comprising:
a plate formed of transducer material and having opposed first and second surfaces with first and second side faces and first and second end faces therebetween, the first and second surfaces being provided with respective first and second electrode layers,
an electrical cable comprising a plurality of parallel conductors, connected electrically to the first electrode layer by a single contact extending generally transversally to the cable over a width of the plate,
wherein the plate is provide with grooves extending along the first surface from the first end face to the second end face, the grooves extending through the first electrode layer and into the transducer material to a depth sufficient to divide the plate into an array of n transducer elements, each having an individual first electrode and sharing a common second electrode, the grooves extending through the single contact to also separate each conductor from an adjacent conductor, whereby each conductor is connected to a respective individual first electrode.

2. Transducer array according to embodiment 1, wherein the transducer material comprises a piezoelectric material selected from titanates, bulk piezo material, piezocomposite material, active piezoelectric material, such as lead zirconate titanate (PZT) (Pb[Zr$_x$Ti$_{1-x}$]O$_3$ 0≤x≤1), AlN, (PbMg$_{0.33}$Nb$_{0.67}$)$_{1-x}$(PbTiO$_3$)$_x$, preferably with x=0.28-

0.5 (PMNT), Cobalt MNT, ceramic and crystalline material, a microelectromechanical system (MEMS), such as a CMUT and PMUT, and combinations thereof.

3. Transducer array according to embodiment 1 or 2, wherein the plate has a thickness of 0.1-2 mm, preferably 0.3-1.0 mm.

4. Transducer array according to any of embodiments 1 to 3, wherein the plate has a surface area of from 10 mm2 to 1000 mm2, preferably between 20 mm2 and 600 mm2, most preferably between 60 mm2 and 500 mm2.

5. Transducer array according to any of embodiments 1-4, wherein the single contact comprises solder, metal, conductive glue or a capacitive coupled contact.

6. Transducer array according to any of embodiments 1-5, wherein the grooves separating the respective transducer elements have a width of 0.01-1 mm, such as 0.05 mm.

7. Transducer array according to any of embodiments 1-6, wherein the grooves separating the respective transducer elements extend to a depth corresponding to 50-95% of the thickness of the plate.

8. Transducer array according to any of embodiments 1-7, further comprising a ground contact extending from the second electrode layer to the first surface of the plate across the first side face and electrically connected to the individual first electrode of the transducer element adjacent to the first side face.

9. Transducer array according to any of embodiments 1-8, wherein the single contact is connected to the first electrode layer adjacent to the first end face and preferably extends less than 5 mm, preferably less than 2 mm but more than 0.2 mm in the direction of the second end face.

10. Transducer array according to any of embodiments 1-9, further comprising a polymer casing, preferably of ABS or polycarbonate, and wherein a thickness of the casing at a side where ultrasound is transmitted is from 0.05-5 mm or 0.05 to 2 mm.

11. Transducer array according to any of embodiments 1-10, wherein the first surface of the plate is provided with a protective layer that gives mechanical stiffness and/or serves as an acoustical backing layer.

12. Transducer array according to any of embodiments 1-11, wherein the array comprises from 10 to 1024 transducer elements, preferably from 12 to 256 transducer elements, more preferably from 14 to 128 transducer elements, 16 to 64 transducer elements or 20 to 32 transducer elements or 24 to 32 transducer elements.

13. Transducer array according to any of embodiments 1-12, further comprising a secondary separation extending transversally with respect to the grooves across the second surface from the first side face to the second side face whereby the second electrode layer is split in two halves and preferably, half of the second electrode layer is connected to a first conductor and the other half of the second electrode layer is connected to a further conductor, to allow separate activation of the two halves.

14. Transducer array according to embodiment 13, comprising one or more secondary separations that extend from the second surface, through the transducer material to a depth sufficient to divide each transducer element into m sections, having common individual first electrodes and separate second electrodes.

15. Transducer array according to embodiment 14, wherein the secondary separations extend more than 50% or more than 90% or more than 95% through the plate.

16. Transducer array according to embodiment 15, wherein the secondary separations extend completely through the plate but not through the first electrode layer, and the sections are angled with respect to each other, preferably by between 1 degree and 15 degrees.

17. Transducer array according to any of embodiments 1-16, further comprising an electrical circuit for supply of signals for driving the transducer elements, the electrical circuit being in electrical connection with the transducer elements via the electrical cable.

18. Ultrasound device comprising a transducer array according to embodiment 17, wherein the electrical circuit comprises transmission control electronics for beam steering of the array as a phased array.

19. Ultrasound device according to embodiment 18, comprising at least one high-voltage pulse source, linked to a low-voltage timing circuit for timing of the at least one high-voltage pulse source.

20. Ultrasound device according to any of embodiments 18 or 19, comprising, receiving control electronics wherein less than 50%, preferably less than 20% of the n transducer elements are connected or connectable to the receiving control electronics.

The invention claimed is:

1. A transducer for ultrasound, comprising:
a one-dimensional transducer array of piezoelectric material comprising at least n transducer elements extending only in a first array direction, wherein n≥8, wherein adjacent transducer elements are provided with at least partial first separations therebetween,
a flexible cable comprising at least n conductors, individually electrically connected to the respective at least n transducer elements by a self-aligned electrical contact, whereby the at least partial first separations between adjacent transducer elements comprise cuts extending through the piezoelectric material and also through the self-aligned electrical contact,
an electrical circuit, for supply of signals for driving the transducer elements, in electrical connection with respective conductors of the flexible cable, and
a casing for the transducer array, in which casing the transducer array is provided.

2. The transducer according to claim 1, wherein each individual transducer element comprises a piezoelectric material selected from titanates, bulk piezo material, piezo-composite material, active piezoelectric material, lead zirconate titanate (PZT) (Pb[ZrxTi1-x]O3 0≤x≤1), AlN, (PbMg0.33Nb0.67)1-x(PbTiO3)x, Cobalt MNT, ceramic and crystalline material, a Microelectromechanical system (MEMS), such as a CMUT, and PMUT, and combinations thereof.

3. The transducer according to claim 2, wherein the transducer element material has a thickness of 0.1 mm to 2 mm.

4. The transducer according to claim 1, wherein at least one transducer element is provided with a conducting material for electrical contact or wherein the self-aligned electrical contacts to the flex cable are soldered contacts, conductive glued contacts, or capacitive coupled contacts.

5. The transducer according to claim 1, wherein the cuts have a width of 0.01 mm to 1 mm, and extend through 50% to 95% of an element thickness.

6. The transducer according to claim 1, wherein a ground contact is provided which extends from a contact at a bottom side of the transducer array, along at least one side of the transducer array, to at least one part of the contact on a top side of the transducer array.

7. The transducer according to claim 1, wherein the casing comprises a polymer, and wherein a thickness of the casing at a side of the transducer array where ultrasound is transmitted is from 0.05 mm to 2 mm, or wherein the other side of the transducer array is protected by a layer over the transducer array that gives mechanical stiffness, protects the transducer array in the casing or serves as an acoustical backing layer.

8. The transducer according to claim 1, wherein the casing comprises space holders for determining a thickness of a matching layer, or wherein the casing is part of an ultrasound path, an acoustical layer, an acoustical matching layer, an acoustical lens, or an acoustical prism.

9. The transducer according to claim 1, further comprising:
   transmission control electronics for beam steering of the transducer array comprising at least one high-voltage pulse source, wherein the source is linked to a low-voltage timing circuit for timing of the at least one pulse source, and
   receiving control electronics operational to limit energy consumption when processing received ultrasound.

10. The transducer of claim 9, further comprising a positioner for maintaining the transducer in a position on a body or a contacting means for contacting the product to a skin of the body and wherein the transducer is a wearable device or a portable device, for signaling a change in a body tissue, body vessel or body cavity.

11. The transducer of claim 9, wherein at least one ultrasound receiving transducer element is adapted for determining ultrasound energy in connection with a rectifying amplifier and the rectifying amplifier is in connection with an analogue adder for adding the outputs of the rectifying amplifiers; or
   wherein the transducers elements are capable of operating separately, sequentially, in phase-shift mode, in parallel mode, in frequency scan mode, in spatial scan mode, in intensity mode, in pulsed mode, in harmonic mode, variations thereof, or combinations thereof.

12. A method of determining or monitoring a liquid volume in a cavity of a body, the method comprising:
   attaching the transducer of claim 9 to a surface of the body adjacent to the cavity;
   operating the transmission control electronics to cause the transducer elements to generate and steer a beam of ultrasound towards the cavity at a frequency of 20 kHz-50 MHz; and
   operating the receiving control electronics to determine ultrasound energy received from the cavity.

13. The transducer of claim 9, wherein less than 50%, of the n transducer elements are connected or connectable to the receiving control electronics.

14. The transducer according to claim 1, further comprising:
   an energy scavenger, an ADC for converting analogue array signals to digitized output signals or a movement sensor, an accelerometer, a gyroscope or a magnetic movement sensor.

15. A method of producing the transducer of claim 1, comprising
   providing a plate of transducer material with first and second electrode layers on respective first and second surfaces,
   providing at least n conductors in a flexible cable, wherein n ≥8,
   at one side of the plate forming, preferably by soldering, a single contact with the ends of the conductors and over a width of the plate while maintaining the temperature of the plate below 220° C., preferably at 10° C. or more below a temperature at which de-poling of the transducer material may occur,
   dividing the transducer material into an array of at least n transducer elements by providing at least n−1, at least partial, separations at a side of the soldering, wherein the separations fully extend through the soldering thereby dividing the single contact into n separate self-aligned contacts, each contact being in connection with an individual conductor of the flexible cable, and
   placing the transducer array in a casing, and fixating the transducer array in the casing.

16. The method according to claim 15, wherein a first surface of the transducer array is protected by layer over the transducer array for providing mechanical stiffness, protection of the transducer in the casing, and as an acoustical backing layer, or wherein the single contact has a width of 0.2 mm to 2 mm, or wherein the single contact is applied on the ends of a flex cable, and/or wherein the transducer material is cooled during soldering.

17. The method according to claim 15, wherein the single contact is formed by soldering and the soldering is applied during less than 10 seconds.

18. The method according to claim 15, wherein after forming the single contact but before dividing the transducer material, the ends of the connecting cables are bent downwards out of the cutting path.

19. The method according to claim 15, wherein a ground contact is provided which extends from the second electrode layer at the second surface of the plate, along at least one side of the plate, to at least one electrode on the first surface of the plate, wherein the at least one electrode is in electrical contact with at least one of the conductors of the flexible cable.

20. A transducer for ultrasound, comprising:
   a transducer array of piezoelectric material comprising at least n transducer elements in a first array direction, wherein n>8, wherein adjacent transducer elements are provided with at least partial first separations therebetween,
   a flexible cable comprising at least n conductors, individually electrically connected to the respective at least n transducer elements by a self-aligned electrical contact, whereby the at least partial first separations between adjacent transducer elements comprise cuts extending through the piezoelectric material and also through the self-aligned electrical contact,
   an electrical circuit, for supply of signals for driving the transducer elements, in electrical connection with respective conductors of the flexible cable, and
   a casing for the transducer array, in which casing the transducer array is provided, wherein the transducer array comprises from 10 to 1024 transducer elements, wherein at least one transducer element is at least partly provided with a secondary separation at an opposite side with respect to the first separations, perpendicular to the first separations, and with a secondary separation length of <90% of the first separation length, or a $p^{th}$ fraction of $p≥3$ of the electrode length is connected to a $p^{th}$ electrode connector, perpendicular to a length direction of the transducer elements.

* * * * *